(12) United States Patent
Bennett et al.

(10) Patent No.: US 7,102,043 B2
(45) Date of Patent: Sep. 5, 2006

(54) PROCESS FOR SYNTHESIZING DIISOPROPYLBENZENE

(75) Inventors: Ronald Quentin Bennett, Tallmadge, OH (US); Jeffrey Alan Goodwin, Fairlawn, OH (US); Jonathan David Rich, Akron, OH (US)

(73) Assignee: The Goodyear Tire + Rubber Company, Akron, OH (US)

( * ) Notice: Subject to any disclaimer, the term of this patent is extended or adjusted under 35 U.S.C. 154(b) by 385 days.

(21) Appl. No.: 10/688,724

(22) Filed: Oct. 17, 2003

(65) Prior Publication Data

US 2005/0075522 A1  Apr. 7, 2005

Related U.S. Application Data

(60) Provisional application No. 60/427,018, filed on Nov. 18, 2002, provisional application No. 60/426,525, filed on Nov. 15, 2002, provisional application No. 60/423,487, filed on Nov. 4, 2002.

(51) Int. Cl.
*C07C 2/66* (2006.01)
*C07C 5/22* (2006.01)

(52) U.S. Cl. .................... 585/323; 585/319
(58) Field of Classification Search ........... 585/323, 585/319
See application file for complete search history.

(56) References Cited

U.S. PATENT DOCUMENTS

| | | | | |
|---|---|---|---|---|
| 3,763,259 A * | 10/1973 | Hervert | .................... | 585/314 |
| 3,832,449 A | 8/1974 | Rosinski et al. | ............ | 423/328 |
| 4,016,218 A | 4/1977 | Haag et al. | ................. | 585/467 |
| 4,418,235 A * | 11/1983 | Haag et al. | ................. | 585/407 |
| 5,902,917 A | 5/1999 | Collins et al. | .............. | 585/323 |

FOREIGN PATENT DOCUMENTS

GB  809908 A  *  3/1959

* cited by examiner

*Primary Examiner*—Thuan-Dinh Dang
(74) *Attorney, Agent, or Firm*—Alvin T. Rockhill

(57) ABSTRACT

This invention relates to a process for synthesizing para-diisopropylbenzene utilizing only cumene and propylene as raw materials. This synthesis technique offers the advantage of eliminating benzene as a raw material used in the process. The elimination of benzene is beneficial because it simplifies the process and eliminates the need to purchase and store benzene for use in the synthesis. The elimination of benzene from the synthesis is of particular value since the use of benzene in industrial applications has been under attack on the basis of environmental, safety, and health concerns. The present invention discloses a process for producing para-diisopropylbenzene from cumene and propylene, said process comprising the steps of (1) introducing a feed stream into an alkylation zone wherein said feed stream is comprised of cumene and propylene, and wherein said alkylation zone contains an alkylation catalyst; (2) allowing the cumene and propylene in the feed stream to react together to produce a first mixture of para-diisopropylbenzene and meta-diisopropylbenzene; (3) fractionally distilling the mixture of para-diisopropylbenzene and meta-diisopropylbenzene in a fractional distillation step to separate the meta-diisopropylbenzene from the para-diisopropylbenzene; (4) isomerizing the meta-diisopropylbenzene in the presence of a transalkylation catalyst to produce a second mixture of para-diisopropylbenzene and meta-diisopropylbenzene; (5) recycling the second mixture of para-diisopropylbenzene and meta-diisopropylbenzene recovered from the transalkylation step to the fractional distillation step; and (6) recovering the para-diisopropylbenzene that was separated from the meta-diisopropylbenzene by the fractional distillation step.

18 Claims, No Drawings

PROCESS FOR SYNTHESIZING DIISOPROPYLBENZENE

This application claims the benefit of U.S. Provisional Patent Application Serial No. 60/423,487, filed on Nov. 4, 2002, U.S. Provisional Patent Application Serial No. 60/426,525, filed on Nov. 15, 2002, and U.S. Provisional Patent Application Serial No. 60/427,018, filed on Nov. 18, 2002.

BACKGROUND OF THE INVENTION

Para-diisopropylbenzene is a valuable organic chemical compound that is currently used on a large scale industrially in the production of para-dihydroxybenzene (hydroquinone) and other aromatic compounds. Para-diisopropylbenzene can be produced by a number of different chemical processes. One such process that has achieved a significant degree of commercial success involves the alkylation of cumene with propylene in the presence of an alkylation catalyst. This alkylation process produces a mixture of para-diisopropylbenzene and meta-diisopropylbenzene. The alkylation catalyst used is selected to preferentially produce para-diisopropylbenzene. However, in commercial practice the alkylation still produces a diisopropylbenzene monomer mixture containing about 25 percent meta-diisopropylbenzene (based upon total diisopropylbenzene isomers) as an unwanted by-product.

In commercial practice the unwanted meta-diisopropylbenzene is reacted with benzene in a transalkylation reaction to produce cumene which is recycled back to the alkylation step. This commercial process of the prior art can be depicted as follows:

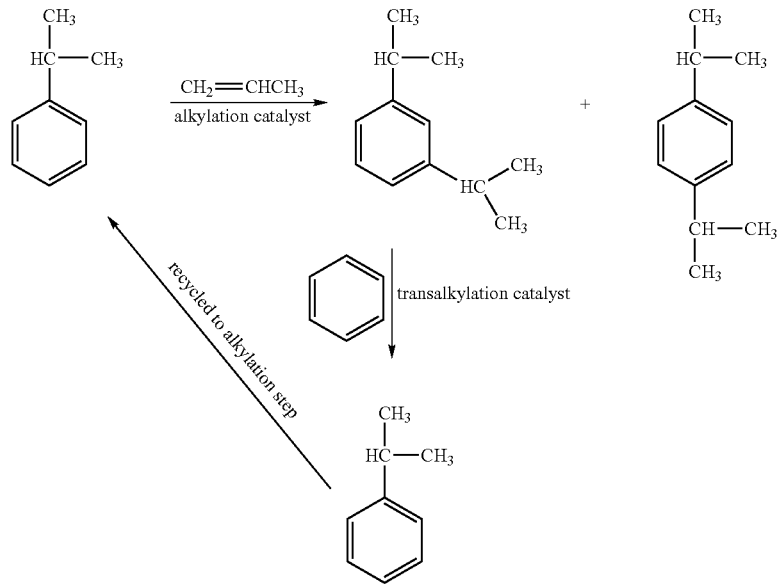

In this prior art process the para-diisopropylbenzene is separated from the meta-diisopropyl benzene by fractional distillation and collected as the desired product of the reaction. The undesired meta-diisopropylbenzene is transalkylated with benzene to produce cumene with is recycled back to the alkylation step. As can be seen, the prior art process calls for cumene, propylene, and benzene as raw materials. However, it would be highly desirable to eliminate benzene from the process. This is because it would no longer be necessary to purchase and store it for use in the synthesis of para-diisopropylbenzene benzene. The elimination of benzene from the synthesis process is of particular value since the use of benzene in industrial applications has been under attack on the basis of environmental, safety, and health concerns.

SUMMARY OF THE INVENTION

The present invention relates to a process for synthesizing para-diisopropylbenzene that utilizes only cumene and propylene as raw materials. The implementation of this process completely eliminates the need to use benzene in the synthesis. Accordingly, the process of this invention is of great commercial value because it provides a commercially viable technique for producing para-diisopropylbenzene without the need for benzene.

The present invention more specifically discloses a process for producing para-diisopropylbenzene from cumene and propylene, said process comprising the steps of (1) introducing a feed stream into an alkylation zone wherein said feed stream is comprised of cumene and propylene, and wherein said alkylation zone contains an alkylation catalyst; (2) allowing the cumene and propylene in the feed stream to react together to produce a mixture of para-diisopropylbenzene and meta-diisopropylbenzene; (3) fractionally distilling the mixture of para-diisopropylbenzene and meta-diisopropylbenzene in a first fractional distillation step to separate the meta-diisopropylbenzene from the para-diisopropylbenzene; (4) isomerizing the meta-diisopropylbenzene in the presence of a transalkylation catalyst to produce a second mixture of para-diisopropylbenzene and meta-diisopropylbenzene; (5) fractionally distilling the second mixture of para-diisopropylbenzene and meta-diisopropylbenzene produced by the isomerization step in a second fractional distillation step to separate the para-diisopropylbenzene from the meta-diisopropylbenzene; (6) recycling the meta-diisopropylbenzene recovered from the second fractional distillation to step 4; and (7) recovering the para-diisopropylbenzene that was separated from the meta-diisopropylbenzene by the first fractional distillation step and the second fractional distillation step.

The present invention also discloses a process for producing para-diisopropylbenzene from cumene and propylene, said process comprising the steps of (1) introducing a feed stream into an alkylation zone wherein said feed stream is comprised of cumene and propylene, and wherein said alkylation zone contains an alkylation catalyst; (2) allowing the cumene and propylene in the feed stream to react together to produce a mixture of para-diisopropylbenzene and meta-diisopropylbenzene; (3) fractionally distilling the mixture of para-diisopropylbenzene and meta-diisopropylbenzene in a first fractional distillation step to separate the meta-diisopropylbenzene from the para-diisopropylbenzene; (4) mixing the meta-diisopropylbenzene recovered from the first fractional distillation with additional cumene to produce a meta-diisopropylbenzene/cumene feed stream; (5) transalkylating the meta-diisopropylbenzene in the meta-diisopropylbenzene/cumene feed stream in the presence of a transalkylation catalyst to produce a second mixture of para-diisopropylbenzene and meta-diisopropylbenzene; (6) fractionally distilling the second mixture of para-diisopropylbenzene and meta-diisopropylbenzene produced by the transalkylation step in a second fractional distillation step to separate the para-diisopropylbenzene from the meta-diisopropylbenzene; (7) recycling the meta-diisopropylbenzene recovered from the second fractional distillation to step 4; and (8) recovering the para-diisopropylbenzene that was separated from the meta-diisopropylbenzene by the first fractional distillation step and the second fractional distillation step.

The subject invention also reveals a process for producing para-diisopropylbenzene from cumene and propylene, said process comprising the steps of (1) introducing a feed stream into an alkylation zone wherein said feed stream is comprised of cumene and propylene, and wherein said alkylation zone contains an alkylation catalyst; (2) allowing the cumene and propylene in the feed stream to react together to produce a first mixture of para-diisopropylbenzene and meta-diisopropylbenzene; (3) fractionally distilling the mixture of para-diisopropylbenzene and meta-diisopropylbenzene in a fractional distillation step to separate the meta-diisopropylbenzene from the para-diisopropylbenzene; (4) isomerizing the meta-diisopropylbenzene in the presence of a transalkylation catalyst to produce a second mixture of para-diisopropylbenzene and meta-diisopropylbenzene; (5) recycling the second mixture of para-diisopropylbenzene and meta-diisopropylbenzene recovered from the isomerization step to the fractional distillation step; and (6) recovering the para-diisopropylbenzene that was separated from the meta-diisopropylbenzene by the fractional distillation step.

The subject invention further reveals a process for producing para-diisopropylbenzene from cumene and propylene, said process comprising the steps of (1) introducing a feed stream into an alkylation zone wherein said feed stream is comprised of cumene and propylene, and wherein said alkylation zone contains an alkylation catalyst; (2) allowing the cumene and propylene in the feed stream to react together to produce a first mixture of para-diisopropylbenzene and meta-diisopropylbenzene; (3) fractionally distilling the mixture of para-diisopropylbenzene and meta-diisopropylbenzene in a fractional distillation step to separate the meta-diisopropylbenzene from the para-diisopropylbenzene; (4) mixing the meta-diisopropylbenzene recovered from the fractional distillation with additional cumene to produce a meta-diisopropylbenzene/cumene feed stream; (5) transalkylating the meta-diisopropylbenzene in the meta-diisopropylbenzene/cumene feed stream in the presence of a transalkylation catalyst to produce a second mixture of para-diisopropylbenzene and meta-diisopropylbenzene; (6) recycling the second mixture of para-diisopropylbenzene and meta-diisopropylbenzene recovered from the transalkylation step to the fractional distillation step; and (7) recovering the para-diisopropylbenzene that was separated from the meta-diisopropylbenzene by the fractional distillation step.

DETAILED DESCRIPTION OF THE INVENTION

Synthesis of Para-Diisopropylbenzene

In the first step of the process of this invention, cumene is alkylated with propylene to produce a mixture of para-diisopropylbenzene (p-DIPB) and meta-diisopropylbenzene (m-DIPB). This alkylation step will be conducted in the presence of an alkylation catalyst. In cases where p-DIPB is being sought, the alkylation will preferably be conducted in the presence of an alkylation catalyst that preferentially produces p-DIPB (results in the production of a high ratio of p-DIPB to m-DIPB). In cases where m-DIPB is being sought, the alkylation will preferably be conducted in the presence of an alkylation catalyst that preferentially produces m-DIPB (results in the production of a high ratio of m-DIPB to p-DIPB).

Various alkylation catalysts that can be used in the practice of this invention are described in U.S. Pat. No. 5,902,917. The teachings of U.S. Pat. No. 5,902,917 are incorporated herein by reference. In any case, the alkylation catalysts that can be used in the practice of this invention include acidic solid oxides. The acidic solid oxides that can be used include aluminosilicates and materials that contain elements other that silicon and aluminum. These acidic solid oxides can be amorphous or crystalline materials. These crystalline materials may have non-layered, 3-dimensional framework structures or the layered structures of clays. The acidic solid oxides that can be employed include super acids formed by modifying zirconia with tungstates or sulfates. The acidic solid oxides that are preferred for utilization in the practice of this invention are zeolites, particularly, medium-pore and large-pore size zeolites.

It is highly preferred to utilize medium pore zeolite catalysts having a Constraint Index that is within the range of 2 to 12 as defined in U.S. Pat. No. 4,016,218 as the alkylation catalyst. Zeolite ZSM-12 is a highly preferred medium pore size alkylation catalyst that can be utilized in the practice of this invention. Zeolite ZSM-12 has a silicon to aluminum ratio of 310 and has a monoclinic cell parameters of a=24.88±0.04 Å, b=5.02±0.02 Å, c=12.15±0.03 Å, and β=107.7±0.1°. Zeolite ZSM-12 is described in greater detail in U.S. Pat. No. 3,832,449. The teachings of U.S. Pat. No. 3,832,449 are incorporated herein by reference.

The alkylation step is typically conducted by introducing a feed stream containing cumene and propylene into an alkylation zone containing the alkylation catalyst. A molar ratio of cumene to propylene of about 4:1 to about 12:1 will typically be employed. A molar ratio of cumene to propylene of about 5:1 to about 10:1 will preferably be employed and a molar ratio of cumene to propylene of about 6:1 to about 8:1 will most preferably be employed. The alkylation reaction will normally be carried out at a temperature that is within the range of about 300° F. (149° C.) to about 400° F. (204° C.) and will preferably be conducted at a temperature this is within the range of 340° F. (171° C.) to about 375° F. (191° C.). The alkylation will more preferably be conducted at a temperature of about 345° F. (174° C.) to about 360° F. (182° C.). As a general rule, the temperature of the alkylation reaction will be increased as the catalyst ages.

The alkylation will typically be conducted under a pressure of 50 psig ($4.5 \times 10^5$ Pascals) to 1000 psig ($7.0 \times 10^6$ Pascals) and will more typically be conducted at a pressure within the range of 300 psig ($2.2 \times 10^6$) to 850 psig ($6.0 \times 10^6$ Pascals). However, the alkylation reaction will normally be conducted under sufficient pressure to maintain the propylene in the liquid state. The alkylation step will normally be carried out utilizing a weight hour space velocity (WHSV) that is within the range of about 2 $hr^{-1}$ to about 10 $hr^{-1}$ and will preferably be conducted using a WHSV which is within the range of 4 $hr^{-1}$ to 8 $hr^{-1}$. The WHSV will most preferably be within the range of about 6.0 $hr^{-1}$ to about 6.5 $hr^{-1}$.

The alkylation reaction will typically result in the production of a diisopropylbenzene isomer mixture containing about 75 percent p-DIPB and 25 percent m-DIPB. This mixture is then fractionally distilled to remove the p-DIPB from the m-DIPB and other reaction by-products. The p-DIPB that is recovered is collected as the intended product of the alkylation reaction.

In practicing the process of this invention, the m-DIPB is isomerized into a mixture of p-DIPB and m-DIPB. This step is conducted in the presence of a transalkylation catalyst and results in the formation of an isomerized mixture containing about 75 to 80 percent p-DIPB and about 20 to 25 percent m-DIPB. The isomerization step can optionally be conducted in the presence of cumene. The p-DIPB produced results from the transalkylation of m-DIPB with cumene to p-DIPB and the isomerization of m-DIPB to p-DIPB. The molar ratio of cumene to m-DIPB fed into the isomerization step will normally be within the range of about 0.01:1 to about 10:1. The molar ratio of cumene to m-DIPB fed into the isomerization step will typically be within the range of about 0.25:1 to about 6:1. The molar ratio of cumene to m-DIPB fed into the isomerization zone will more typically be within the range of about 0.5:1 to about 4:1. The molar ratio of cumene to m-DIPB fed into the isomerization zone will most typically be about 1:1.

The transalkylation catalysts that can be used in the isomerization step include the same general classes of materials that can be used as the alkylation catalyst. In any case, the transalkylation catalysts that can be used in the practice of this invention include acidic solid oxides. The acidic solid oxides that can be used include aluminosilicates and materials that contain elements other than silicon and aluminum.

These acidic solid oxides can be amorphous or crystalline materials. These crystalline materials may have non-layered, 3-dimensional framework structures or the layered structures of clays. The acidic solid oxides that can be employed include super acids formed by modifying zirconia with tungstates or sulfates. The acidic solid oxides that are preferred for utilization in the practice of this invention are zeolites, particularly, medium-pore and large-pore size zeolites.

It is highly preferred to utilize medium pore zeolite catalysts having a Constraint Index that is within the range of 2 to 12 as defined in U.S. Pat. No. 4,016,218 as the transalkylation catalyst in the practice of this invention to attain a high ratio of p-DIPB to m-DIPB and to minimize the formation of triisopropyl benzenes, such as 1, 3, 5-triisopropyl benzene and 1, 2, 4-triisopropyl benzene. Zeolite ZSM-12 is a highly preferred medium pore size alkylation catalyst that can be utilized in the practice of this invention as the transalkylation catalyst. Zeolite ZSM-12 has a silicon to aluminum ratio of 310 and has a monoclinic cell parameters of a=24.88±0.04 Å, b=5.02±0.02 Å, c=12.15±0.03 Å, and β=107.7±0.1°. Zeolite ZSM-12 is described in greater detail in U.S. Pat. No. 3,832,449. The teachings of U.S. Pat. No. 3,832,449 are incorporated herein by reference.

The isomerization step is typically conducted in an isomerization zone containing the transalkylation catalyst. The isomerization step can optionally be conducted by introducing a feed stream containing cumene and m-DIPB into the isomerization zone containing the transalkylation catalyst. The isomerization reaction will normally be carried out at a temperature that is within the range of about 350° F. (182°) to about 460° F. (238° C.) and will preferably be conducted at a temperature that is within the range of 365° F. (185° C.) to about 430° F. (221° C.). The isomerization will more preferably be conducted at a temperature of about 380° F. (193° C.) to about 415° F. (213° C.). As a general rule, the temperature of the transalkylation reaction will be increased as the catalyst ages.

The transalkylation will typically be conducted under a pressure of 50 psig ($4.5 \times 10^5$ Pascals) to 1000 psig ($7.0 \times 10^6$ Pascals) and will more typically be conducted at a pressure within the range of 300 psig ($2.2 \times 10^6$ Pascals) to 800 psig ($5.6 \times 10^6$ Pascals). However, the transalkylation reaction will normally be conducted under sufficient pressure to maintain the cumene in the liquid state. The transalkylation step will normally be carried out utilizing a weight hour space velocity (WHSV) that is within the range of about 0.5 $hr^{-1}$ to about 10 $hr^{-1}$ and will preferably be conducted using a WHSV which is within the range of 1 $hr^{-1}$ to 8 $hr^{-1}$. The WHSV will most preferably be within the range of about 1.5 $hr^{-1}$ to about 6 $hr^{-1}$.

The mixture of p-DIPB and m-DIPB produced in the isomerization step is fractionally distilled to remove the p-DIPB from the m-DIPB and any cumene that may be present. The p-DIPB is recovered as the desired reaction product and the m-DIPB and optionally cumene are recycled back to the isomerization step (transalkylation step if cumene is present). A schematic diagram of the process of this invention can be depicted as follows:

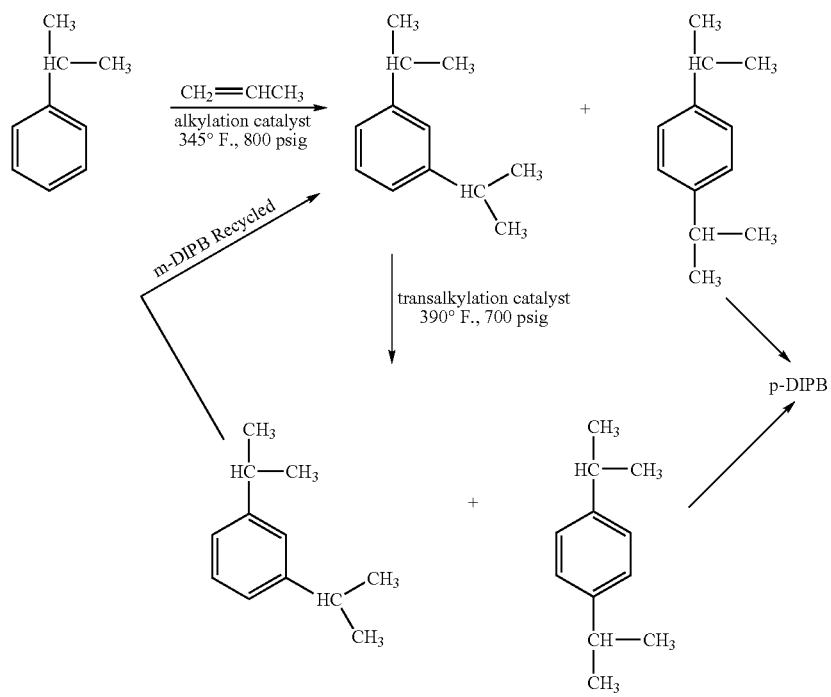

Synthesis of Meta-Diisopropylbenzene

In is also possible to preferentially synthesize and recover m-DIPB by utilizing another embodiment of this invention. For instance, in some cases it might be desirable to produce m-DIPB rather than p-DIPB. This would be the situation in cases where resorcinol was the ultimate chemical compound desired rather than hydroquinone. The procedure used to synthesize and recover m-DIPB is similar to the one used in making and recovering p-DIPB. This embodiment of the invention more specifically relates to a process for producing meta-diisopropylbenzene from cumene and propylene, said process comprising the steps of (1) introducing a feed stream into an alkylation zone wherein said feed stream is comprised of cumene and propylene, and wherein said alkylation zone contains an alkylation catalyst; (2) allowing the cumene and propylene in the feed stream to react together to produce a first mixture of para-diisopropylbenzene and meta-diisopropylbenzene; (3) fractionally distilling the mixture of para-diisopropylbenzene and meta-diisopropylbenzene in a fractional distillation step to separate the para-diisopropylbenzene from the meta-diisopropylbenzene; (4) isomerizing the para-diisopropylbenzene in the presence of a transalkylation catalyst to produce a second mixture of para-diisopropylbenzene and meta-diisopropylbenzene; (5) recycling the second mixture of para-diisopropylbenzene and meta-diisopropylbenzene recovered from the isomerization step to the fractional distillation step; and (6) recovering the meta-diisopropylbenzene that was separated from the para-diisopropylbenzene by the fractional distillation step. It should be noted that cumene can optionally be added to the isomerization step.

In the preferred synthesis of m-DIPB, an alkylation catalyst that produces a higher ratio of m-DIPB to p-DIPB will be used in the alkylation step. In such a scenario, Zeolite MCM-22 could be used as both the alkylation and transalkylation catalyst. In this alternative embodiment of the invention, after the fractional distillation step, the p-DIPB is mixed with cumene and transalkylated into a mixture of m-DIPB and p-DIPB.

Zeolite MCM-22 has structure that consists of two independent, non-interconnecting channel systems, each accessible through 10-ring apertures. One of these pore systems is defined by two-dimensional sinusoidal channels. The other is comprised of super cages whose inner free diameter (7.1 Å) is defined by 12-rings and whose inner height is 18.2 Å. Zeolite MCM-22 is described in greater detail in Michael E. Leonowicz, Jeffrey A. Lawton, Stephen L. Lawton, and Mae K. Rubin, "MCM-22: A Molecular Sieve with Two Independent Multidimensional Channel Systems," Science, Volume 264, pages 1910–1913 (24 Jun. 1994), the teachings of which are incorporated herein by reference in their entirety.

A schematic diagram of this process of for producing m-DIPB can be depicted as follows:

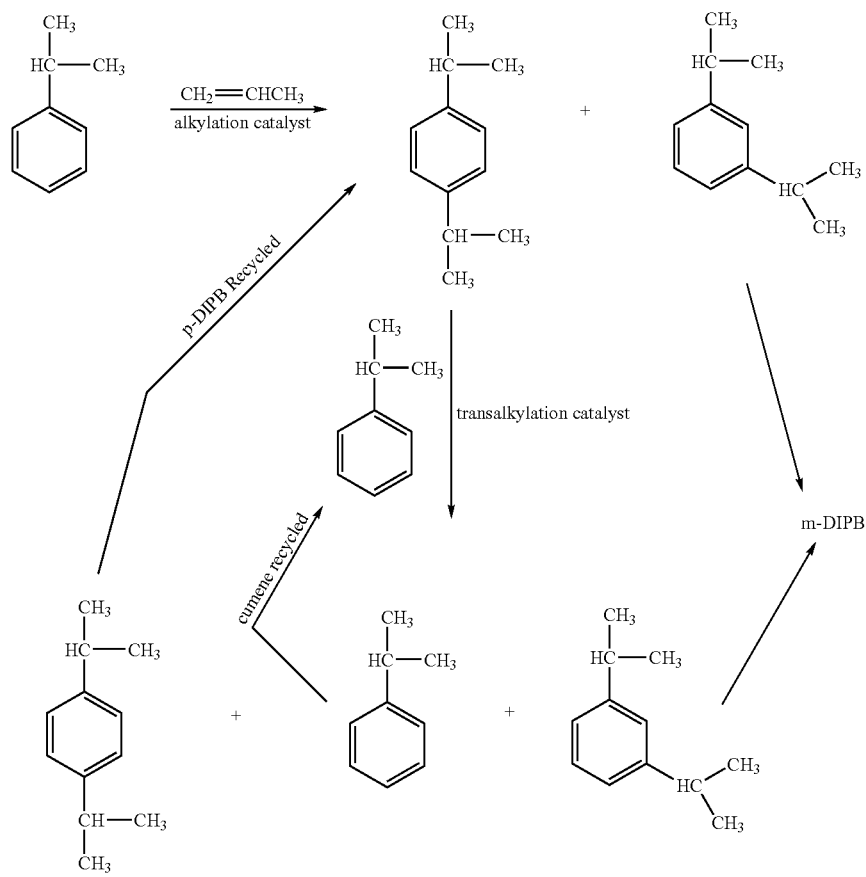

In the schematic diagram depicted above, cumene is added to the p-DIPB that is isomerized into a mixture of m-DIPB and p-DIPB. It is not necessary to add cumene to the p-DIPB before isomerization. However, cumene can optionally be added as shown. Unreacted cumene is then recycled to the isomerization step or can optionally be recycled to the alkylation step.

This invention is illustrated by the following examples which are merely for the purpose of illustration and are not to be regarded as limiting the scope of the invention or the manner in which it can be practiced. Unless specifically indicated otherwise, all parts and percentages are given by weight.

EXAMPLE 1

In this experiment, p-DIPB was synthesized by utilizing the technique of this invention. In the procedure used, 142 g (195 cc) of silica alumina catalyst, consisting of 90% silica and 10% alumina, was loaded into a 24" long 1.0"OD (0.83" ID) 316 stainless steel tube. The catalyst bed was positioned for optimal heating within the reactor by supporting and retaining the bed on inert packing. The reactor was heated externally with hot-oil spiral-wound heat tracing (0.25" OD tubing). A m-DIPB stream (consisting of 98.5% m-DIPB, 0.6% o-DIPB, 0.2% p-DIPB, with the balance being m-, o-, and p-ethylcumenes) was fed to the reactor at a rate of 4.0 g/minute, resulting in a space velocity of 1.7 WHSV's. Pressure was maintained at 700 psig by a back pressure controller. The reactor was heated to 392° F. and the contents were allowed to come to steady state. Sample #1 was collected and analyzed by GC. The temperature was then raised to 419° F. and the contents were allowed to come to steady state. Sample #2 was collected and analyzed by GC. The temperature was then raised to 455° F. and the contents were allowed to come to steady state. Sample #3 was collected and analyzed by GC. The results are reported in the table below.

In the catalyst loading procedure used, a stainless steel screen was positioned at the bottom of the reactor. Then about 1/8–1/4" of glass wool was packed next on top of the screen, followed by the catalyst. Finally, about 10 cc of glass chips were loaded on top of the catalyst bed, followed by another plug of glass wool. The feed stream was fed with vertical downflow and was operated liquid-full.

| Run | Feed | 1 | 2 | 3 |
|---|---|---|---|---|
| Temp (deg F.) | | 392 | 419 | 455 |
| Flow Rate (g/min) | | 4.0 | 4.0 | 4.0 |
| WHSV | | 1.7 | 1.7 | 1.7 |
| Component (Wt %) | | | | |
| Cumene | | 1.0 | 3.2 | 9.9 |
| m-DIPB | 98.5 | 92.8 | 81.9 | 55.9 |
| o-DIPB | 0.6 | 0.5 | 0.4 | 0.4 |
| p-DIPB | 0.2 | 3.3 | 8.1 | 15.2 |
| 1,3,5-TIPB | | 1.2 | 4.5 | 14.5 |
| 1,2,4-TIPB | | 0.4 | 0.8 | 1.4 |
| % m- in m/p-DIPB | | 97 | 91 | 79 |
| % p- in m/p-DIPB | | 3 | 9 | 21 |

-continued

| Run | Feed | 1 | 2 | 3 |
|---|---|---|---|---|
| % m-DIPB Conversion | | 6 | 17 | 43 |
| Selectivity to p-DIPB, Wt % Basis | | 57 | 48 | 35 |
| Selectivity to cumene, p-DIPB, & TIPB's | | 102 | 99 | 95 |

EXAMPLE 2

In this experiment, m-DIPB was synthesized utilizing the technique of this invention. In the procedure used, 142 grams (195 cc) of silica alumina catalyst, consisting of 90% silica and 10% alumina, was loaded into a 24" long 1.0" OD (0.83" ID) 316 stainless steel tube. The catalyst bed was positioned for optimal heating within the reactor by supporting and retaining the bed on inert packing. The reactor was heated externally with hot-oil spiral-wound heat tracing (0.25" OD tubing). p-DIPB stream (consisting of 99.4% p-DIPB, 0.1% m-DIPB, with the balance being various hexylbenzene isomers) was fed to the reactor at 4.0 g/minute, resulting in a space velocity of 1.7 WHSV's. Pressure was maintained at 700 psig by a back pressure controller. The reactor was heated to 392° F. and the contents were allowed to come to steady state.

Sample #1 was collected and analyzed by GC. The temperature was then raised to 419° F. and the contents were allowed to come to steady state. Sample #2 was collected and analyzed by GC. The temperature was then raised to 455° F. and the contents were allowed to come to steady state. Sample #3 was collected and analyzed by GC. The results are reported in the table below.

In the catalyst loading procedure used, a stainless steel screen was positioned at the bottom of the reactor. Then about 1/8–1/4" of glass wool was packed next on top of the screen, followed by the catalyst. Finally, about 10 cc of glass chips were loaded on top of the catalyst bed, followed by another plug of glass wool. The feed stream was fed with vertical downflow and was operated liquid-full.

| Run | Feed | 1 | 2 | 3 |
|---|---|---|---|---|
| Temp (deg F.) | | 392 | 419 | 455 |
| Flow Rate (g/min) | | 4.0 | 4.0 | 4.0 |
| WHSV | | 1.7 | 1.7 | 1.7 |
| Component (Wt %) | | | | |
| Cumene | | 2.6 | 5.4 | 11.4 |
| m-DIPB | 0.1 | 8.3 | 16.0 | 28.1 |
| o-DIPB | | 0.1 | 0.3 | 0.4 |
| p-DIPB | 99.4 | 84.3 | 68.9 | 40.0 |
| 1,3,5-TIPB | | 2.9 | 7.1 | 15.4 |
| 1,2,4-TIPB | | 1.3 | 1.5 | 1.8 |
| % m- in m/p-DIPB | | 9 | 19 | 41 |
| % p- in m/p-DIPB | | 91 | 81 | 59 |
| % p-DIPB Conversion | | 15 | 31 | 60 |
| Selectivity to m-DIPB, Wt % Basis | | 55 | 52 | 47 |
| Selectivity to cumene, m-DIPB, & TIPB's | | 99 | 98 | 95 |

While certain representative embodiments and details have been shown for the purpose of illustrating the subject invention, it will be apparent to those skilled in this art that various changes and modifications can be made therein without departing from the scope of the subject invention.

What is claimed is:

1. A process for producing para-diisopropylbenzene from cumene and propylene, said process consisting of the steps of (1) introducing a feed stream into an alkylation zone wherein said feed stream is comprised of cumene and propylene, and wherein said alkylation zone contains an alkylation catalyst; (2) allowing the cumene and propylene in the feed stream to react together to produce a first mixture of para-diisopropylbenzene and meta-diisopropylbenzene; (3) fractionally distilling the mixture of para-diisopropylbenzene and meta-diisopropylbenzene in a fractional distillation step to separate the meta-diisopropylbenzene from the para-diisopropylbenzene; (4) isomerizing the meta-diisopropylbenzene in the presence of a catalyst to produce a second mixture of para-diisopropylbenzene and meta-diisopropylbenzene; (5) recycling the second mixture of para-diisopropylbenzene and meta-diisopropylbenzene recovered from the isomerization step to the fractional distillation step; and (6) recovering the para-diisopropylbenzene that was separated from the meta-diisopropylbenzene by the fractional distillation step; wherein said process is void of benzene; and wherein the meta-diisopropylbenzene is isomerized in step (4) in the absence of cumene.

2. A process for producing para-diisopropylbenzene as specified in claim 1 wherein the isomerization step is conducted at a temperature which is within the range of about 350° F. to about 460° F.

3. A process for producing para-diisopropylbenzene as specified in claim 1 wherein the alkylation step is conducted at a temperature that is within the range of about 300° F. to about 400° F.

4. A process for producing para-diisopropylbenzene as specified in claim 1 wherein the catalyst utilized in the isomerization step is an acidic solid oxide catalyst.

5. A process for producing para-diisopropylbenzene as specified in claim 1 wherein the catalyst utilized in the isomerization step is a zeolite catalyst.

6. A process for producing para-diisopropylbenzene as specified in claim 1 wherein the catalyst utilized in the isomerization step is zeolite ZSM-12.

7. A process for producing para-diisopropylbenzene as specified in claim 1 wherein the alkylation catalyst is an acidic solid oxide catalyst.

8. A process for producing para-diisopropylbenzene as specified in claim 1 wherein the alkylation catalyst is a zeolite catalyst.

9. A process for producing para-diisopropylbenzene as specified in claim 1 wherein the alkylation catalyst is zeolite ZSM-12.

10. A process for producing para-diisopropylbenzene as specified in claim 1 wherein the isomerization step is conducted at a temperature which is within the range of about 365° F. to about 430° F.

11. A process for producing para-diisopropylbenzene as specified in claim 10 wherein the alkylation step is conducted at a temperature that is within the range of about 340° F. to about 375° F.

12. A process for producing para-diisopropylbenzene as specified in claim 11 wherein the catalyst utilized in the isomerization step is a zeolite catalyst.

13. A process for producing para-diisopropylbenzene as specified in claim 12 wherein the alkylation catalyst is a zeolite catalyst.

14. A process for producing para-diisopropylbenzene as specified in claim 13 wherein the isomerization step is conducted at a temperature which is within the range of about 380° F. to about 415° F.

15. A process for producing para-diisopropylbenzene as specified in claim 10 wherein the alkylation step is conducted at a temperature which is within the range of about 345° F. to about 360° F.

16. A process for producing para-diisopropylbenzene as specified in claim 15 wherein the catalyst utilized in the isomerization step is zeolite ZSM-12.

17. A process for producing para-diisopropylbenzene as specified in claim 16 wherein the alkylation catalyst is zeolite ZSM-12.

18. A process for producing para-diisopropylbenzene from cumene and propylene, said process consisting of the steps of (1) introducing a feed stream into an alkylation zone wherein said feed stream is comprised of cumene and propylene, and wherein said alkylation zone contains an alkylation catalyst; (2) allowing the cumene and propylene in the feed stream to react together to produce a mixture of para-diisopropylbenzene and meta-diisopropylbenzene; (3) fractionally distilling the mixture of para-diisopropylbenzene and meta-diisopropylbenzene in a first fractional distillation step to separate the meta-diisopropylbenzene from the para-diisopropylbenzene; (4) isomerizing the meta-diisopropylbenzene in the presence of a catalyst to produce a second mixture of para-diisopropylbenzene and meta-diisopropylbenzene; (5) fractionally distilling the second mixture of para-diisopropylbenzene and meta-diisopropylbenzene produced by the isomerization step in a second fractional distillation step to separate the para-diisopropylbenzene from the meta-diisopropylbenzene; (6) recycling the meta-diisopropylbenzene recovered from the second fractional distillation to step 4; and (7) recovering the para-diisopropylbenzene that was separated from the meta-diisopropylbenzene by the first fractional distillation step and the second fractional distillation step: wherein said process is void of benzene; and wherein the meta-diisopropylbenzene is isomerized in step (4) in the absence of cumene.

* * * * *